United States Patent
Rosenzweig et al.

(10) Patent No.: US 7,745,001 B2
(45) Date of Patent: Jun. 29, 2010

(54) SYNTHESIS OF NANOASSEMBLIES CONTAINING LUMINESCENT QUANTUM DOTS AND MAGNETIC NANOPARTICLES

(75) Inventors: Zeev Rosenzweig, New Orleans, LA (US); Yongfen Chen, Fayetteville, AR (US); Desheng Wang, Milwaukee, WI (US)

(73) Assignee: University of New Orleans Research and Technology Foundation, Inc., New Orleans, LA (US)

(*) Notice: Subject to any disclaimer, the term of this patent is extended or adjusted under 35 U.S.C. 154(b) by 657 days.

(21) Appl. No.: 11/088,242

(22) Filed: Mar. 23, 2005

(65) Prior Publication Data

US 2010/0112716 A1 May 6, 2010

Related U.S. Application Data

(60) Provisional application No. 60/555,629, filed on Mar. 23, 2004.

(51) Int. Cl.
*B32B 5/16* (2006.01)

(52) U.S. Cl. .......... 428/402; 428/403; 428/407; 435/103; 436/526; 977/773; 977/783; 977/824; 977/830; 977/834; 977/838

(58) Field of Classification Search .......... 428/402, 428/403, 407; 435/103; 436/526; 977/773, 977/783, 824, 830, 834, 838
See application file for complete search history.

(56) References Cited

U.S. PATENT DOCUMENTS

| | | | |
|---|---|---|---|
| 5,961,507 A * | 10/1999 | Widlund | 604/378 |
| 6,322,901 B1 | 11/2001 | Bawendi et al. | |
| 6,447,887 B1 | 9/2002 | Claus et al. | |
| 6,548,171 B1 | 4/2003 | Barbera-Guillem et al. | |
| 6,548,264 B1 * | 4/2003 | Tan et al. | 435/7.21 |
| 6,630,307 B2 | 10/2003 | Bruchez et al. | |
| 6,680,211 B2 * | 1/2004 | Barbera-Guillem et al. | 436/533 |
| 6,699,723 B1 | 3/2004 | Weiss et al. | |
| 6,773,823 B2 | 8/2004 | O'Connor et al. | |
| 6,906,339 B2 * | 6/2005 | Dutta | 257/40 |
| 7,172,791 B2 * | 2/2007 | Treadway et al. | 427/215 |
| 7,214,427 B2 * | 5/2007 | Huang et al. | 428/402 |

(Continued)

OTHER PUBLICATIONS

Salgueirino-Maceira et al., Composite Silica Spheres with Magnetic and Luminescent Functionalities, Adv. Funct. Mater., vol. 16, Issue 4, (2006).*

(Continued)

*Primary Examiner*—H. (Holly) T Le
(74) *Attorney, Agent, or Firm*—Garvey, Smith, Nehrbass & North, L.L.C.; Seth M. Nehrbass

(57) ABSTRACT

Negatively charged luminescent CdSe—ZnS quantum dots (QDs) were successfully incorporated into novel luminescent glyconanospheres averaging around 190 nm in diameter through electrostatic interactions with carboxymethyldextran (CM-dextran) and polylysine. The glyconanospheres preferably contain as well carboxyl-modified iron oxide nanocrystals. In addition to electrostatic attraction between the negatively charged dextran, the negatively charged CdSe—ZnS QDs (and negatively charged iron oxide nanocrystals, if present), and the positively charged polylysine, covalent amide bonds were introduced to cross link the QDs (and negatively charged iron oxide nanocrystals, if present) with the polysaccharide matrix to further stabilize the glyconanospheres. The dextran residues on the surface of the nanospheres show high affinity toward the glucose binding protein-Concanavalin A (Con A). As a result, these luminescent CdSe—ZnS QD incorporated glyconanospheres are a useful tool for studying carbohydrate-protein interactions that are critical steps in bacterial and viral infection.

27 Claims, 7 Drawing Sheets

U.S. PATENT DOCUMENTS

| | | | |
|---|---|---|---|
| 7,261,940 B2 * | 8/2007 | Klimov et al. | 428/403 |
| 7,534,489 B2 * | 5/2009 | Ying et al. | 428/402 |
| 2003/0157327 A1 * | 8/2003 | Barbera-Guillem et al. | 428/402.24 |
| 2003/0178309 A1 * | 9/2003 | Huang et al. | 204/547 |
| 2006/0068203 A1 * | 3/2006 | Ying et al. | 428/403 |
| 2006/0118757 A1 * | 6/2006 | Klimov et al. | 252/62.51 R |

OTHER PUBLICATIONS

Sou-Yee Mak et al.,Fabrication of Magnetic Luminescent Nanocomposites via Adsorption-Precipitation of metal Ions on Sulfonated Iron Oxide Nanoparticles, Chemistry Letter, vol. 35, No. 10, pp. 1116-1117, (2006).*

Dosev et al., Magnetic/luminescent core/shell particles synthesized by spray pyrolysis and their application in immunoassays with internal standard, Nanotechnology 18 (2007) 055102 (6pp).*

Gu et al., "Facile One-Pot Synthesis of Bifunctional Heterodimers of Nanoparticles: A Conjugate of Quantum Dot and Magnetic Nanoparticles", J. Am. chem. Soc. 2004, 126, 5664-5665, (published on Web Apr. 20, 2004).*

Chen et al, Synthesis of Glyconanospheres Containing LUminescent CdSe-ZnS Quantum Dots, Nano Lett., 2003, vol. 3, No. 5, 581-584.*

* cited by examiner

Negatively charged CdSe/ZnS QDs    Positively charged polylysine

Dextran    Negatively charged CM-dextran

SYNTHESIS OF NANOASSEMBLIES CONTAINING LUMINESCENT QUANTUM DOTS AND MAGNETIC NANOPARTICLES

CROSS-REFERENCE TO RELATED APPLICATIONS

Priority of our U.S. Provisional Patent Application Ser. No. 60/555,629, filed 23 Mar. 2004, incorporated herein by reference, is hereby claimed.

STATEMENT REGARDING FEDERALLY SPONSORED RESEARCH OR DEVELOPMENT

This work was supported by the National Science Foundation (NSF) grants CAREER CHE-9874498; NSF/LEQSF2001-04-RII-03; and CHE-0134027.

REFERENCE TO A "MICROFICHE APPENDIX"

Not applicable

BACKGROUND OF THE INVENTION

1. Field of the Invention

The present invention relates to markers. More particularly, the present invention relates to luminescent markers.

2. General Background of the Invention

Luminescent semiconductor quantum dots (QDs) have been intensely studied due to their unique optical properties, including sharp emission spectra with full width at half-maximum (fwhm) as narrow as 25 nm, high photostability, and tunable size dependent emission peaks.[1-5] Incorporation of luminescent semiconductor quantum dots into nanospheres has been explored as a way to prepare bright biological labels and functional composite luminescent materials. For example, Barbera-Guillem successfully encapsulated luminescent CdSe QDs and other metal oxide nanocrystals in nanometric liposomes for potential biological labeling applications.[6] Rogach et al. encapsulated CdSe QDs in 40-80 nm silica nanospheres and proposed to use them as building blocks to form 3D colloid crystal microstructures.[7] Moffitt et al. encapsulated CdS QDs in water-soluble block copolymers to form large compound micelles (LCM) that averaged 65 nm in diameter.[8]

Electrostatic interactions of polyelectrolytes have been widely applied in layer-by-layer procedures to prepare thin films since Decher et al. introduced this unique technique in the early 1990s.[10-11] Using this technique, Anai et al. successfully incorporated the highly charged protein avidin into a thin film and used it to immobilize biotinylated molecules.[12] Caruso et al. immobilized enzymes on the surface of polystyrene microspheres to fabricate micrometric biocatalyst carriers using the same layer-by-layer approach.[13] Goldman et al. prepared bioinorganic conjugates by using negatively charged CdSe—ZnS QDs and positively charged avidin. They used these new particles for luminescence immunoassay applications.[14] In their study, the concentrations of QDs and avidin were limited to minimize aggregation due to electrostatic attractions.

The following U.S. Patents are incorporated herein by reference:

6,773,823 Sequential synthesis of core-shell nanoparticles using reverse micelles 6,699,723 Organo luminescent semiconductor nanocrystal probes for biological applications and process for making and using such probes 6,630,307 Method of detecting an analyte in a sample using semiconductor nanocrystals as a detectable label 6,548,171 Fluorescent nanocrystal-embedded microspheres for fluorescence analyses 6,447,887 Electrostrictive and piezoelectric thin film assemblies and method of fabrication therefor 6,322,901 Highly luminescent color-selective nano-crystalline materials.

The following articles (and all references mentioned herein) are incorporated herein by reference:

Decher, G.; Hong, J. D. Makromol. Chem. Macromol. Symp. 1991, 46, 321;

Decher, G.; Hong, J. D.; Schmitt, J. Thin Solid Films 1992, 210/211, 831;

Caruso, F.; Trau, D.; Mohwald, H.; Renneberg, R.; Langmuir 2000, 16(4), 1485;

Goldman, E. R.; Balighian, E. D.; Mottoussi, H.; Kuno, M. K.; Mauro, J. M.; Tran, P. T.; Anderson, G. P. J. Am. Chem. Soc. 2002, 124, 6378.

BRIEF SUMMARY OF THE INVENTION

The present invention includes a novel method to assemble highly luminescent semiconductor quantum dots (preferably CdSe—ZnS) and magnetic nanoparticles (preferably of iron oxide) into nanoassemblies. The inventors believe that this is the first time that someone has integrated luminescent semiconductor QDs and magnetic nanoparticles in the same nanoassemblies. Existing nanoparticles used in diagnostic applications of which the inventors are aware are either magnetic or luminescent but not both.

The present invention includes a novel technique to prepare luminescent and magnetic nanoassemblies averaging around 200 nm in diameter. The nanoassemblies contain hydrophilic or hydrophobic semiconductor (preferably CdSe—ZnS) quantum dots and magnetic nanoparticles of preferably iron oxide.

Hydrophilic quantum dots and magnetic particles can be encapsulated in glyconanospheres. The underlying principle of this technique is electrostatic interactions between positively charged polylysine molecules and negatively charged particles and carboxymethyldextran molecules. In addition to electrostatic attraction between the particles and the molecules, covalent amide bonds were introduced to cross-link the particles with the polysaccharide matrix to further stabilize the novel nanoassemblies.

Hydrophobic particles can be assembled in silica nanospheres using a microemulsion synthetic method.

The emission properties of the quantum dots-containing nanoassemblies were similar to the emission properties of individual quantum dots despite of the presence of magnetic nanoparticles in the assemblies, although some decrease in emission quantum yield was noted. Assembling hundreds of quantum dots in single nanoassemblies created bright and photostable nanoassemblies that could be easily observed using conventional fluorescence microscopy instrumentation. The encapsulation of magnetic nanoparticles in the nanoassemblies enabled their manipulation and separation from solution using an external magnetic field. The novel nanoassemblies could be used in biological applications requiring magnetic separation and highly sensitive fluorescence detection.

U.S. Pat. No. 6,548,171 discloses polymer microspheres. The particles of the present invention are nanometric, meaning 10-100 times smaller.

The method to load nanocrystals into the microspheres of U.S. Pat. No. 6,548,171 is by swelling and shrinking by changing solvents. The microspheres swell in one solvent which enable nanocrystals to diffuse in, then shrink in water to lock the nanocrystals in. The main problem with this approach is stability. Nanocrystals leak out of the particles when exposed to uncontrolled environments of temperature and acidity.

The method to entrap nanocrystals in the smaller particles of the present invention is different. When trapped in the glyconanospheres the nanocrystals are assembled into covalently bonded structures. They are prepared in one step, unlike the microspheres that are first prepared then loaded with nanocrystals. When trapped in silica nanospheres the nanocrystals are precursors in the microemulsion-based method. Again, the nanocrystals are covalently attached to the formed assemblies. As a result of the covalent attachment the particles of the present invention exhibit higher stability than the microspheres in which the nanocrystals are only encapsulated in through weaker physical interactions.

Since the method used to prepare the polymer microspheres in U.S. Pat. No. 6,548,171 involves swelling and shrinking it appears that the method works only with polymer materials that could swell and shrink readily when placed in different solvents. The glyconanospheres and the silica spheres of the present invention do not swell and shrink in different solvents.

U.S. Pat. No. 6,548,171 mentions that the fluorescence microspheres could have a magnetic core. There are commercially available magnetic polystyrene microspheres that could be loaded with fluorescent nanocrystals to form magnetic and luminescent microspheres. Again, these particles will be micrometric in dimensions and will take several steps to prepare. In contrast, the particles of the present invention are prepared in one step.

The preferred luminescent quantum dots of the present invention are CdSe/ZnS luminescent quantum dots: cadmium selenide nanoparticles that are coated with a zinc sulphide shell. Luminescent quantum dots that have visible emission almost always have cadmium. The counter ion could be different, for example cadmium sulphide (CdS) or cadmium teleride (CdTe). Changing the counter ion changes the emission color. CdS particles emit light at higher energies (still visible but close to the UV range). CdTe nanoparticles emit red light (still visible but close to the infrared region). In almost all cases a shell of ZnS is used to passivate the surface to increase the emission efficiency.

The preferred magnetic nanoparticles of the present invention are iron oxide magnetic nanoparticles (e.g., $\gamma$-$Fe_2O_3$ or $Fe_3O_4$). It is the understanding of the inventors that iron oxide is the only type of magnetic nanoparticles approved for in-vivo biomedical applications because these particles if capped correctly are not toxic. It is possible to form magnetic nanoparticles with superior magnetic properties like metallic cobalt or alloys of iron and gold. The iron-gold alloys could be potentially useful for cell separation applications because they may not be toxic. Cobalt particles are highly toxic (they probably should be banned for environmental concerns).

The glyconanospheres of the present invention can contain dextran molecules (or could contain other polysaccharides) on their surface that interact strongly with carbohydrate binding proteins. These glyconanospheres can be used for real-time monitoring of protein carbohydrate interactions. The inventors in their studies of the present invention focused on lectins, which are sugar binding proteins. In particular the inventors worked with Concanavaline A (Con A) which binds glycosylic residues in carbohydrates with high affinity (the dissociation constant of dextran-Con A was found in studies of the present inventors to be about 1 nanomolar).

The assay of the present invention could be carried out to screen lectins for their binding affinity to glycosylic residues on the surface of the quantum dots-containing glyconanospheres. The rate of aggregation of the glyconanospheres depends on the concentration and the binding affinity of lectins to the glycosylic residues on the surface of the glyconanospheres.

The glyconanospheres (around 200 nm in diameter) of the present invention can advantageously be used for lectin recognition assays. The quantum dots coated magnetic nanoparticles (around 30 nm in diameter) of the present invention can advantageously be used for breast cancer cells separation and detection in blood.

The present invention includes luminescent and magnetic nanoassemblies comprising luminescent semiconductor QDs and magnetic nanoparticles. These nanoassemblies can typically be around 10 nm to 300 nm in diameter. The present invention includes a plurality of the such nanoassemblies, averaging around 200 nm±25 nm in diameter or smaller. These nanoassemblies can include luminescent quantum dots and magnetic nanocrystals assembled in glyconanospheres.

The present invention includes a plurality of these nanoassemblies, which can average around 30 nm±15% in diameter or smaller. These can include nanoassemblies in which luminescent quantum dots of around 1-5 nm in diameter directly coat core magnetic nanoparticles of around 10-20 nm in diameter.

The nanoassemblies of the present invention can average around 20 nm±15% in diameter or smaller.

The nanoassemblies of the present invention can average around 20 nm±15% in diameter.

The nanoassemblies of the present invention preferably comprise luminescent semiconductor Cd-containing QDs and magnetic nanoparticles.

In the nanoassemblies of the present invention, the QDs preferably include a shell of ZnS.

In the nanoassemblies of the present invention, preferably the magnetic nanoparticles are magnetic iron oxide nanoparticles.

The nanoassemblies of the present invention preferably comprise luminescent semiconductor CdSe—ZnS QDs and magnetic iron oxide nanoparticles.

In the nanoassemblies of the present invention, preferably the nanoassemblies are encapsulated in glyconanospheres.

Preferably, the components of the nanoassemblies of the present invention are bound electrostatically. Alternatively, the components of the nanoassemblies of the present invention are bound covalently.

Preferably, the nanoassemblies of the present invention contain molecules on their surface that interact strongly with carbohydrate binding proteins. Preferably, the molecules are dextran molecules.

The nanoassemblies of the present invention preferably comprise QDs bound to the surface of thiol-modified magnetic nanoparticles.

The present invention includes a method of using the nanoassemblies of the present invention for real-time monitoring of protein-carbohydrate interactions, comprising: attaching to the nanoassemblies a protein or carbohydrate to create modified nanoassemblies; exposing the modified nanoassemblies to fluid thought to contain a carbohydrate or protein of interest to allow protein-carbohydrate interactions to occur if the fluid contains the carbohydrate or protein of interest; observing the modified nanoassemblies after the modified nanoassemblies are exposed to the fluid. Preferably, the modified nanoassemblies are separated from the fluid using magnetic force.

The present invention includes a method of using the nanoassemblies of the present invention for detecting cancer cells, comprising: attaching to the nanoassemblies antibodies against membranal biomarkers that are selectively expressed in breast cancer cells to create modified nanoassemblies; exposing the modified nanoassemblies to fluid thought to contain circulating breast cancer cells to allow the modified nanoassemblies to attach selectively to any breast cancer cells through binding of the antibody-modified nanoassemblies to membranal biomarkers on the cancer cells. Preferably, the modified nanoassemblies are separated from the fluid using magnetic force. When the fluid includes blood which contains breast cancer cells, the breast cancer cells bound to the modified nanoassemblies are separated from the blood using magnetic force. Optionally, the modified nanoassemblies can have different emission colors and different antibodies where the emission color would code for a specific antibody, to enable determination of multiple biomarkers on a cell surface.

The present invention includes a method of assembling highly luminescent semiconductor QDs and magnetic nanoparticles into nanoassemblies, comprising: providing highly luminescent semiconductor QDs in chloroform; providing magnetic nanoparticles in water; coupling the QDs to the magnetic nanoparticles in a chloroform/methanol/water mixture. Preferably, the methanol is added to the QD-containing chloroform to form a mixture of methanol and QD-containing chloroform; and the water containing magnetic nanoparticles is injected into the mixture of methanol and QD-containing chloroform under sonication and vigorous stirring. Preferably, the QDs comprise highly luminescent semiconductor CdSe—ZnS and the magnetic nanoparticles comprise iron oxide nanoparticles.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein.

DETAILED DESCRIPTION OF THE INVENTION

Synthesis of Glyconanospheres Containing Luminescent CdSe—ZnS Quantum Dots

The present inventors in their laboratory developed CdSe QDs doped luminescent micelles that were stabilized by a thin silica layer on their surfaces. The stabilized micelles were more stable than ordinary micelles or liposomes.[9] Common disadvantages of these structures have been their lack of surface functional groups that are suitable for further bioconjugation and limited chemical stability and biocompatibility. Here, the present inventors describe the development of CdSe—ZnS QD incorporated luminescent glyconanospheres that are suitable for biomolecule conjugation while maintaining the high emission quantum yield of the QDs. The glyconanospheres preferably contain dextran molecules on their surface that interact strongly with carbohydrate binding proteins (CBP). These novel glyconanospheres could be used for real-time monitoring of protein carbohydrate interactions.

In the study in which the present invention was developed the present inventors used electrostatic interactions to incorporate negatively charged CdSe—ZnS QDs into luminescent nanospheres that contain polysaccharides on their surface. While DNA and protein molecules were already conjugated to luminescent semiconductor quantum dots,[15-16] the present inventors demonstrate the synthesis of QD-polysaccharide nanocomposites. To prepare dextran grafted luminescent nanospheres, negatively charged CM-dextran and CdSe—

ZnS QDs capped with mercaptosuccinic acid were mixed with 80 000 Da positively charged polylysine.

In another study in which the present invention was developed, the present inventors used electrostatic interactions to incorporate negatively charged CdSe—ZnS QDs and iron oxide magnetic nanocrystals into luminescent nanospheres that contain polysaccharides on their surface. While DNA and protein molecules were already conjugated to luminescent semiconductor quantum dots, the present inventors demonstrate for the first time the synthesis of polysaccharide nanocomposites that contain luminescent quantum dots, magnetic nanocrystals and both luminescent quantum dots and magnetic nanocrystals. To prepare dextran grafted luminescent glyconanospheres, negatively charged CM-dextran, CdSe—ZnS QDs capped with mercaptosuccinic acid and carboxyl-modified iron oxide nanocrystals were mixed with 80 000 Da positively charged polylysine.

Figure 1:
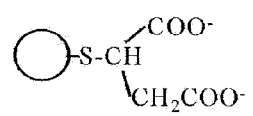
FIG. 1. Structures of negatively charged mercaptosuccinic acid modified CdSe—ZnS QDs, positively charged polylysine, and negatively charged carboxymethyldextran.
Figure 1:
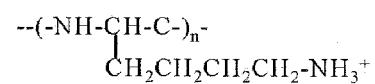
Figure 1:
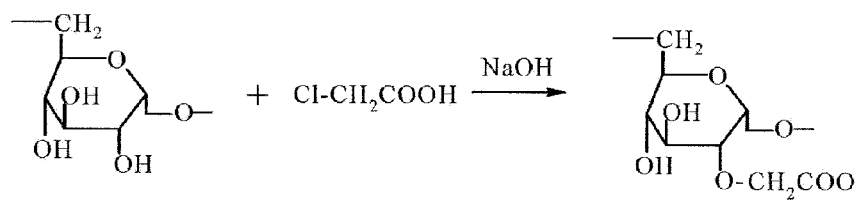

FIG. 1 shows the structures of the precursors used to prepare the luminescent glyconanospheres. CdSe—ZnS core-shell quantum dots (QDs) were synthesized according to a method developed by Hines et al.[2] and Peng et al.[17] 12 mg of CdO were mixed with 200 mg lauric acid at 240° C. under $N_2$ atmosphere. Then, 1.5 g of trioctylphosphine oxide and 1.5 g of 1-hexadecylamine were added to the flask and the temperature was raised to 320° C. Next, a solution of 80 mg Se dissolved in 2 mL trioctylphosphine was quickly injected into the flask. The mixture was kept at this temperature for 3 min. CdSe QDs were then collected by precipitation with anhydrous methanol. To coat the CdSe core with a ZnS shell, 20 mg CdSe QDs and 3 g trioctylphosphine oxide were loaded into a 50 mL flask, then a solution of 70 µL hexamethyldisilathiane and 400 µL 1.0 M diethylzinc in 2 mL trioctylphosphine was injected into the flask at 200° C. The solution was incubated at 120° C. for 3 h. The surface of the QDs was then capped with mercaptosuccinic acid. A 5 mg portion of CdSe—ZnS QDs was dispersed in 30 mL anhydrous methanol that contained 30 mg mercaptosuccinic acid. The pH of the solution was adjusted to 10 by using tetramethylammonium hydroxide. The solution was refluxed at 70° C. for 6 h. Mercaptosuccinic acid capped CdSe—ZnS QDs were collected by precipitation with ether. Each mercaptosuccinic acid molecule contains two carboxylic groups. As a result, the CdSe—ZnS QDs had a high density of negative charges on their surface and were highly water-soluble.

Carboxyl-modified iron oxide nanoparticles were obtained from Indicia Biotech, France.

Figure 2:
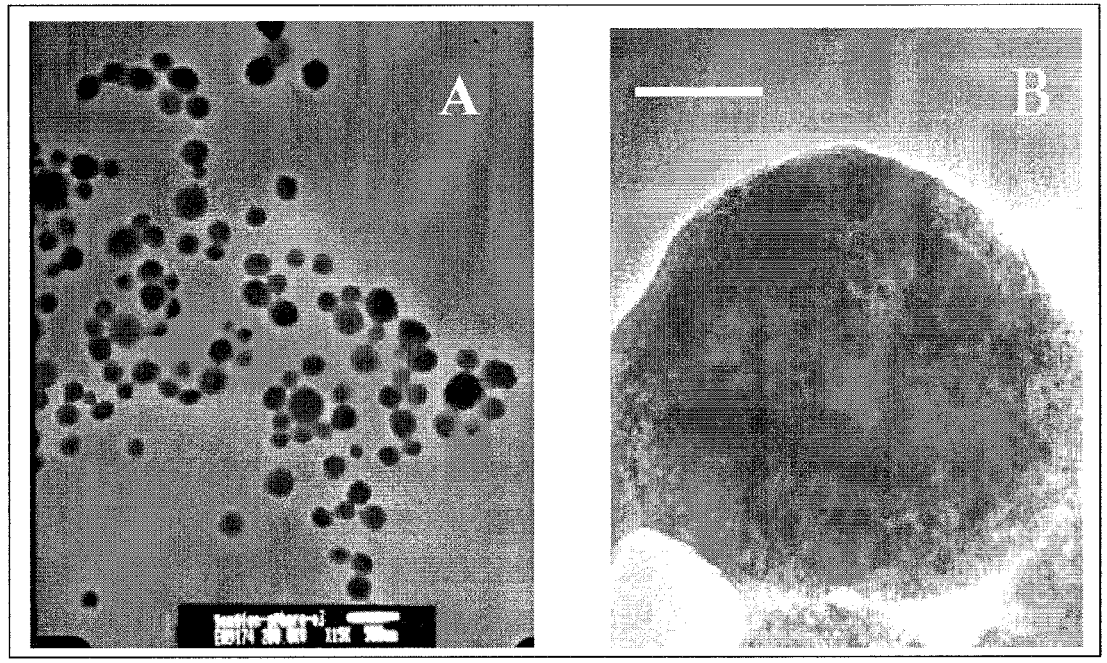
FIG. 2. TEM images of as-prepared luminescent glyconanospheres. (A) 15 000× image of CdSe—ZnS QDs incorporated in luminescent glyconanospheres. The scale bar is 500 nm. (B) 150 000× high-resolution image of a single luminescent glyconanosphere showing that the glycosphere contains many CdSe—ZnS QDs. The scale bar is 50 nm. TEM images are taken using a JEOL 2010 transmission electron microscope. (C) Histogram describing the size distribution of the luminescent glyconanospheres.
Figure 2:
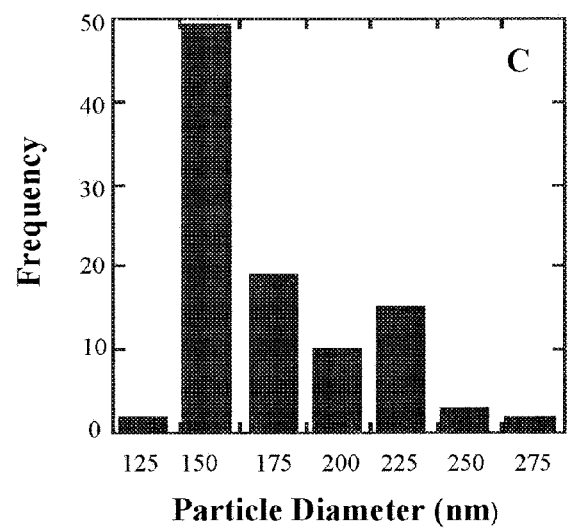

Carboxymethyldextran (CM-dextran) was prepared by mixing 100 mg dextran with a molecular weight of 10 000 Da with 200 mg chloroacetic acid in a 6N NaOH alkaline solution at 60° C. for 1 h following a procedure first suggested by Rebizak et al.[18] To prepare the luminescent glyconanospheres, 300 µL aqueous solution of 500 µM CM-dextran was mixed with 120 µL aqueous solution of 0.19 µL mercaptosuccinic acid modified CdSe—ZnS QDs (when forming QDs containing spheres), 0.19 µL of carboxyl-modified iron oxide nanoparticles (when forming iron oxide containing spheres) and 0.19 µL of CdSe/ZnS QDs and 0.19 µL iron oxide nanoparticles (when forming luminescent/magnetic nanocomposite spheres). The concentration of the CdSe—ZnS QDs was calculated using molecular extinction coefficients previously reported by Striolo et al. of $1.1 \times 10^6$ $M^{-1}$ $cm^{-1}$ for 3 nm sized CdSe—ZnS QDs and $1.22 \times 10^6$ $M^{-1}$ $cm^{-1}$ for 6 nm sized CdSe—ZnS QDs.[19] Then, 120 µl of 10 µM polylysine in a pH 7.0 phosphate buffer solution was added to the CM-dextran and QD containing solution. The reaction mixture was incubated at room temperature for 30 min. The concentration of iron oxide nanoparticles was calculated based on inductive coupled plasma (ICP) atomic absorption measurements that quantified the level of iron per mg sample. The newly formed glyconanospheres were washed three times using centrifugation at 4500 rpm for 15 min to remove unreacted QDs and CM-dextran. FIG. 2A shows a representative TEM image of as-prepared luminescent glyconanospheres. The spherical nanospheres average 190 nm in diameter. FIG. 2B shows a high-resolution TEM image focusing on a single glyconanosphere. The nanometric CdSe—ZnS QDs are clearly seen as darker dots in this image. FIG. 2C shows the size distribution of the luminescent glyconanospheres. Nearly 70% of the glyconanospheres are between 150 and 200 nm in diameter.

Figure 3:
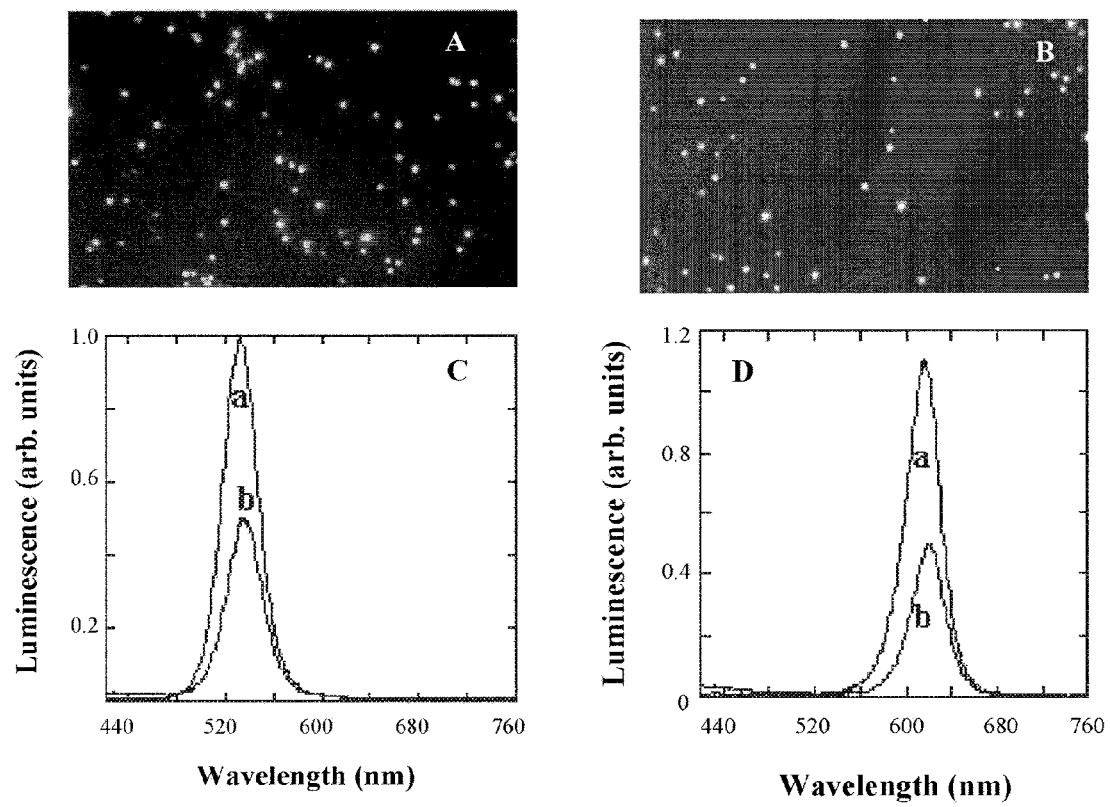
FIG. 3. (A) Luminescence image of negatively charged green emission CdSe—ZnS QDs incorporated glyconanospheres. (B) Luminescence image of negatively charged red emission CdSe—ZnS QD incorporated glyconanospheres. (C) Emission spectra of free green emission QDs (curve a) and glyconanospheres containing green emission QDs (curve b). (D) Emission spectra of free red emission QDs (curve a) and glyconanospheres containing red emission QDs (curve b). The luminescence images were taken using a digital fluorescence imaging microscopy system equipped with an intensified charge coupled device camera (ICCD). The excitation wavelength was 470 nm and the magnification of the microscope was 40×. Emission spectra were taken using a Quanta Master PTI fluorometer.

Since this preparation method is based on electrostatic interactions, the size of the QDs should not affect the formation of the nanospheres (small variations in the size of the quantum dots or magnetic nanocrystals did not affect the formation of the larger glyconanospheres). Indeed, QDs of different diameter and different emission color were incorporated into the luminescent glyconanospheres. FIGS. 3A and 3B show digital luminescence microscopy images of green and red emission QDs containing glyconanospheres. The glyconanospheres are highly luminescent with a signal-to-noise ratio (S/N) of over 100. FIGS. 3C and 3D compare between the emission spectra of solutions containing green and red emission CdSe—ZnS QDs and the spectra of solutions of glyconanospheres incorporating CdSe—ZnS QDs. The emission band of the incorporated QDs is similar to the emission band of free QDs but still shows a 4 nm redshift. This minor red shift may be attributed to a change of surface charge states of the QDs. The intensity differences result from different concentrations of emitting particles and not from a decreased emission quantum yield.

The dextran molecules play an important role in forming the spherical nanospheres and preventing their aggregation.

Figure 4:
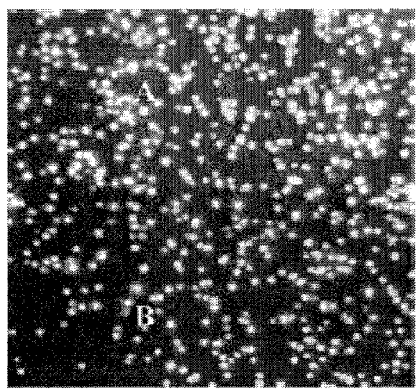
FIG. 4. Luminescence images of Oregon green and CdSe—ZnS containing glyconanospheres. The upper half of the image (4A) is dominated by the green emission of Oregon Green. The lower half of the image (4B) shows the image of the red emission of the glyconanospheres following 3 min irradiation at 470 nm, which effectively bleaches the Oregon Green molecules.

To prove that dextran molecules are indeed incorporated into the nanospheres, the present inventors prepared glyconanospheres with Oregon Green labeled dextran molecules. Oregon-Green is a highly luminescent green dye with fluorescein-like emission properties ($\lambda ex=470$ nm, $\lambda em=525$ nm). It also provides one negative charge for each dye molecule that is attached to the dextran polymeric chain. When excited at 470 nm, the glyconanospheres showed bright green emission due to the emission of Oregon green (FIG. 4A). Following illumination of the sample for about 3 min, the emission of the glyconanospheres turned red (the emission color of the QDs) due to rapid photobleaching of the Oregon green molecules (FIG. 4B). These experiments confirmed that the dextran molecules are indeed integrated with CdSe—ZnS QDs in the same glyconanospheres.

Unlike the strong attraction of polyelectrolytes often observed in thin films formed on a flat surface using the layer-by-layer deposition technique, the present inventors found that electro-static interactions solely are not strong enough to stabilize the luminescent glyconanospheres. Fluorescence microscopy measurements revealed that these luminescent glyconanospheres dissociated in about 10 h when stored in aqueous solution at room temperature. The relative instability of the electrostatically held glyconanospheres could be attributed to their large surface-to-volume ratio. The interactions of solution ions with surface charges weaken the electrostatic attraction between the positively charged polylysine and the negatively charged CM-dextran, and the mercaptosuccinic acid modified CdSe QDs. To further stabilize the luminescent glyconanospheres, the present inventors introduced the standard water-soluble bioconjugate coupling agent 1-ethyl-3-(3)-dimethylamino-propyl carbodiimide (EDC) to initiate the formation of covalent bonds between the carboxylic groups on the surface of the mercaptosuccinic acid modified CdSe QDs and in the CM-dextran chains and the amino groups of the polylysine chains. The concentration of EDC was 500 mM. The reaction mixture was incubated at room temperature for 2 hours. The formation of amide bonds between the carboxylic and amino groups in the glyconanospheres greatly increased their chemical stability. Luminescence microscopy measurements revealed that the covalently and electrostatically held glyconanospheres remained stable for over two months when stored in aqueous solution at room temperature.

Figure 5:
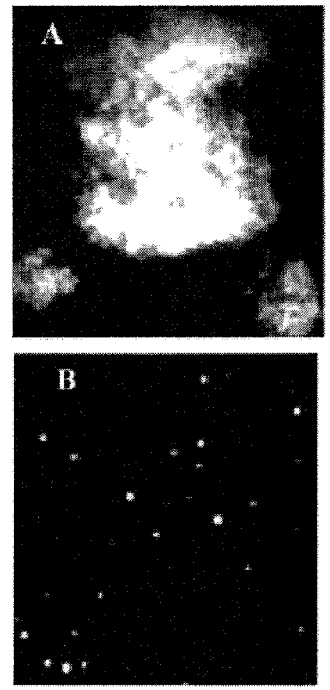
FIG. 5. Lectin Con A initiated aggregation of dextran bound CdSe—ZnS QD incorporated luminescent glyconanospheres. (A) Luminescence image of aggregated glyconanospheres in the presence of Con A. (B) Luminescence image of the glyconanospheres in the presence of Con A and free R-D-glucose. The R-D-glucose molecules compete with the glyconanospheres on the Con A binding sites and prevent aggregation.
Figure 6:
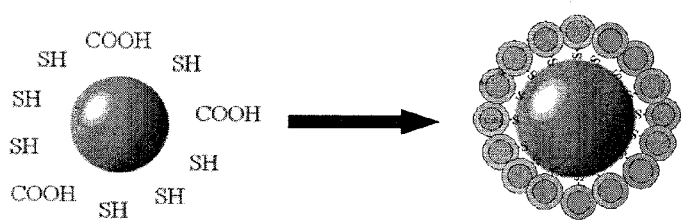
FIG. 6. Thiol and carboxy modified $\gamma$-$Fe_2O_3$ beads are reacted with CdSe/ZnS QDs to form the luminescent/magnetic nanocomposite particles.

CM-dextran provides the glyconanospheres with high surface density of glucosylic residues. Thus, the carbohydrate binding protein concanavalin A (Con A) can recognize the surface bound dextran. Con A is a lectinic protein that selectively binds to the terminal residues of R-D-glucose and R-D-mannose. Each Con A molecule contains four binding sites for carbohydrates.[20] These polyvalent binding sites have been often used in cell agglutination and separation of glycoproteins in affinity chromatography.[21] To demonstrate the binding interactions of the surface-bound dextran and Con A, the present inventors mixed a solution of 200 μL 0.04 μM (based on the concentration of CdSe—ZnS QDs) glyconanospheres with 2 mL 0.05M HEPES buffer solution (pH 7.2) containing 0.25 mg/mL Con A, 0.1 mM $Mn^{2+}$, and 0.1 mM $Ca^{2+}$. The solution was incubated at room temperature for 2 h. FIG. 5A shows the luminescence images of the glyconanospheres following the addition of Con A. Aggregation of the glyconanospheres due to multiple binding with Con A molecules is clearly seen. The aggregation rate depended on the Con A and glyconanospheres concentrations. The aggregation of glyconanospheres was prevented by the addition of 15 mg free R-D-glucose to the solution, since glucose effectively competes with the glyconanospheres on the binding sites of Con A.

The present inventors have developed a novel method to assemble highly luminescent semiconductor CdSe—ZnS QDs into glyconanospheres through electrostatic interactions and covalent stabilization. The present inventors have also developed a novel method to assemble highly luminescent semiconductor CdSe—ZnS QDs and iron oxide nanocrystals into glyconanospheres through electrostatic interactions and covalent stabilization. The emission properties of the QDs containing glyconanospheres were similar to the emission properties of individual QDs. Assembling hundreds of QDs in single glyconanospheres created bright and photostable particles that could be easily observed using conventional fluorescence microscopy instrumentation. This could make luminescent QDs more accessible to fluorescence microscopy studies of biological samples. For example, the luminescent glyconanospheres showed high affinity to Con A, a glucose specific lectin. As demonstrated herein, these glyconanospheres could be used to study carbohydrate-protein interactions.

Superparamagnetic Fe2O3 Beads-CdSe/ZnS Quantum Dots Core-Shell Nanocomposite Particles for Cell Separation A preferred embodiment of the present invention includes the formation of luminescent and magnetic nanocomposite particles that consist of superparamagnetic core particles ($\gamma$-$Fe_2O_3$) and a layer of luminescent CdSe/ZnS quantum dots (QDs) on their surface. These particles could be used in a variety of biomedical and biological applications including magnetic separation and detection of cancer cells, bacteria and viruses. CdSe semiconductor quantum dots (QDs) with diameters ranging between 1.5 and 8 nm exhibit strong, tunable luminescence.[22-26] They have been widely investigated for their size-dependent optoelectronic properties,[27] and for their potential use in optical devices,[28] biological labels,[29] and sensors.[30] Luminescent QDs are brighter, exhibit higher photostability and show narrower emission peaks compared to organic fluorophores.[29] CdSe QDs are often coated with a layer of ZnS, which has a larger band gap, to passivate their surface and to increase their emission quantum yield through quantum confinement.[31] To enable miscibility of the QDs in aqueous solution, their surface has been modified with carboxyl functional groups.[32] Alternatively, QDs were encapsulated in water miscible shells such as liposomes,[33] silica miscelles,[34] and glyconanospheres.[35] QDs were also encapsulated in dendrimers[36,37] to increase their stability against photooxidation and photobleaching.

Luminescent CdSe/ZnS QDs of green emission and red emission colors were synthesized based on a method developed by Peng et al., with minor modifications.[25] 12.7 mg cadmium oxide and 160 mg lauric acid were mixed in a 100 mL three-neck flask. The mixture was heated to ~200° C. in a mantle to fully dissolve the cadmium oxide in the lauric acid solution. Then, 1.94 g trioctylphosphine oxide (TOPO) and 1.94 g hexadecylamine (HDA) were added to the solution. The mixture was heated to a temperature higher than 280° C. and kept under a dry nitrogen atmosphere. Upon reaching the desirable temperature the mantle was removed and 2 mL trioctylphosphine (TOP) solution containing 80 mg selenium powder was rapidly injected into the solution under vigorous stirring. It was previously shown that the diameter of the formed QDs depends on the reaction temperature with smaller particles formed at higher temperature.[22] The color of the mixture changed from clear colorless to yellow, orange, or red depending on the exact temperature. To form a ZnS coating on the CdSe QDs, the mixture was cooled to ~200° C. Then, after being kept three minutes at this temperature, a solution containing 250 μl hexamethyldisllathiane (($TMS)_2$S) and 1 mL diethylzinc ($Zn(Et)_2$) premixed in 2 mL TOP was gradually injected into the solution over a minute. The reaction mixture was kept at 180° C. and stirred for 1 h. The solution was cooled to room temperature and the resulting sample of CdSe/ZnS QDs was washed three times with methanol and chloroform. The QDs showed extremely high quantum yield, reaching 100%. The present inventors even can see the shining fluorescence under room light.

Polymer coated $\gamma$-$Fe_2O_3$ superparamagnetic magnetic beads were purchased from Indicia Biotech, France. The nanometric $\gamma$-$Fe_2O_3$ magnetic particles were coated with dimercapto-succinimid acid (DMSA) to stabilize and functionalize the ferrofluid. The surface of the ferrofluid was covered with free thiol (SH) and carboxyl (COOH) residues (3:20 thiol to COOH ratio) to enable covalent coupling of various ligands to the magnetic particles.[38] A TEM image (FIG. 7a) of the polymer coated particles shows that their magnetic core averages 10±15% nm in diameter. The hydrodynamic diameter of the particles that include the polymer layer was found to be around 20±10% nm based on dynamic light scattering measurements. The particles were fully miscible in aqueous solution and no aggregation was observed.

The coupling between the luminescent CdSe/ZnS QDs and the magnetic beads was based on thiol chemistry. Thiols (—SH) are probably the most utilized functional groups for stabilizing and modifying CdSe QDs.[32,36,37,39,40] Thiol groups form stable bonds with metals on the surface of QDs such as cadmium and zinc.[41-45] However, the coupling reaction between the QDs and magnetic beads presented a difficulty since the trioctylphosphine oxide (TOPO) capped CdSe/ZnS QDs were dissolved in chloroform while the polymer-coated magnetic beads were dispersed in water. The present inventors found that running the coupling reaction in a 10:5:1 mixture of chloroform/methanol/water yielded the best nanocomposite particles with minimal aggregation. To carry out the coupling reaction the present inventors first transferred 1 mL of 1 µM CdSe/ZnS QDs into a 5 mL vial. Then the present inventors added 500 µl methanol to the solution. This was followed by the slow injection of 100 µl 0.1 µM magnetic bead-water suspension to the solution under sonication and vigorous stirring. Under these reaction conditions the molar ratio between the QDs and the magnetic particles was 100:1. The excess of QDs was imperative to preventing aggregation of the magnetic beads. Under vigorous stirring the aqueous and organic phases formed an even suspension. The suspension was stirred for 1 h to form the nanocomposite particles. The luminescent/magnetic nanoparticles were then separated from the solution by using a permanent magnet (average cross sectional force density 16.6 $T^2/m$) and washed several times with methanol. The sample was vortexed briefly and sonicated for 15 min to prevent aggregation.

Figure 7:
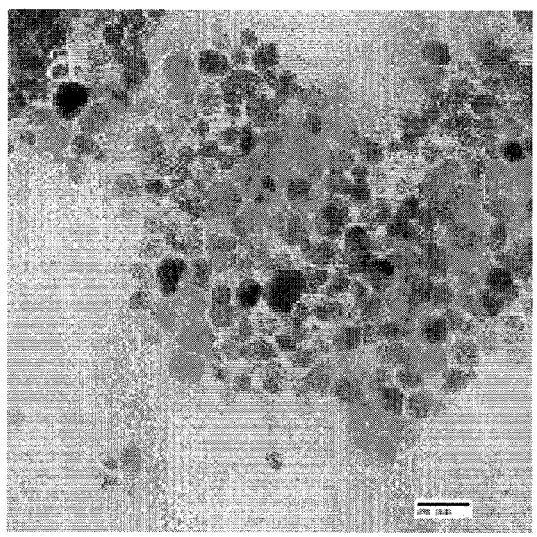
FIG. 7. (a) A TEM image of magnetic beads ($\gamma$-$Fe_2O_3$) coated with a functionalized polymer; the scale bar is 20 nm. (b) A TEM image of QD-magnetic beads core-shell nanoparticles. The scale bar is 20 nm. (c) A High-resolution TEM image of a single magnetic bead coated with quantum dots. The scale bar is 5 nm.
Figure 7:
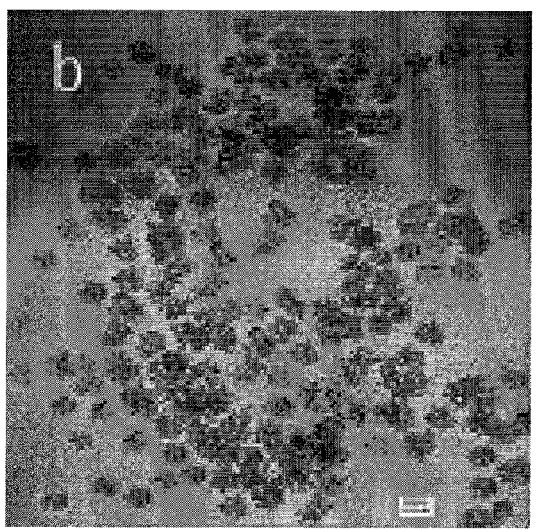
Figure 7:
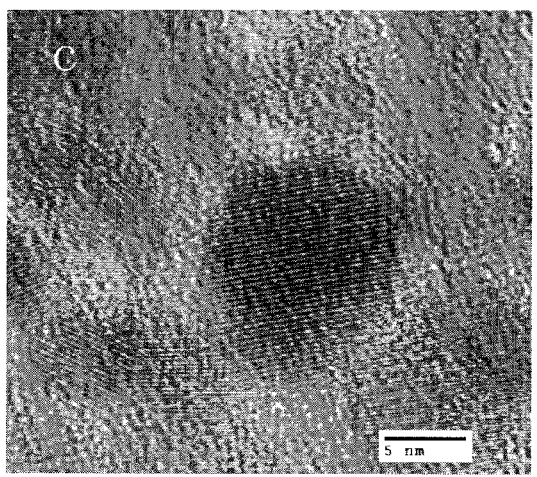
Figure 8:
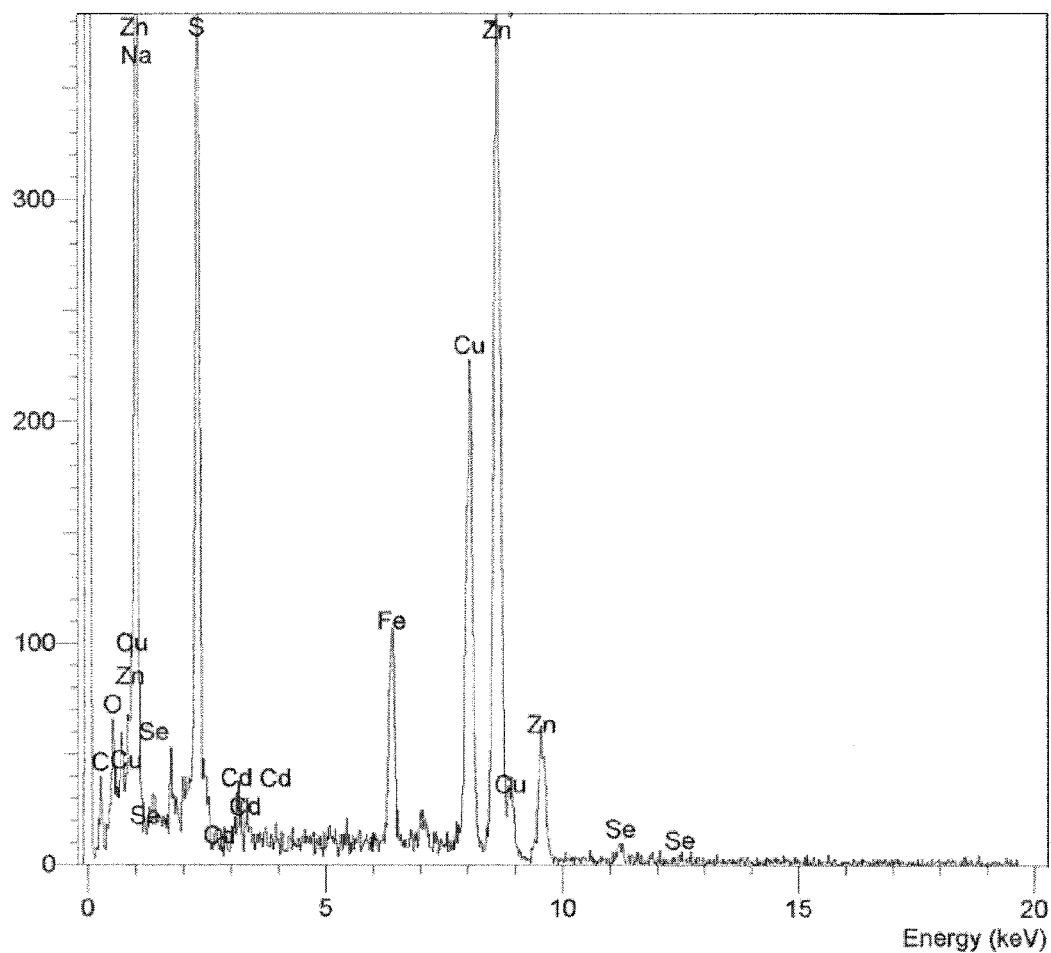
FIG. 8. EDS (energy disperse spectroscopy) spectrum of a single magnetic bead-QDs core-shell particle.

A representative TEM image of the nanocomposite particles is shown in FIG. 7b. The particles average 20 nm in diameter with a size distribution of about 15% and show minimal or no aggregation. Assuming the magnetic beads are fully covered with QDs, the maximum number of QDs per magnetic bead could be estimated based on the following equation:

$$N = 2\pi(R_{Fe} + R_{QD})^2 / \sqrt{3} R_{QD}^2$$

where $R_{Fe}$ is the radius of the magnetic beads and $R_{QD}$ is the radius of the smaller QDs. This estimated expression is derived by dividing the surface area covered by the small QDs on the larger iron oxide particle by the area covered by a single QD on the iron oxide particle surface. The calculation assumes close packing of QDs on the magnetic particle surface and takes into consideration the gaps between the QDs. For example, for a magnetic particle diameter of 10 nm, the maximum number of QDs increases from 45 to 133 when the QD diameter decreases from 4 to 2 nm. A high-resolution TEM image of an individual magnetic bead coated with CdSe/ZnS QDs is shown in FIG. 7c. Gaps between the QDs can be seen, which indicates imperfect coating. It also implies that the number of QDs per magnetic particle would be lower than the upper theoretical limit. An energy dispersed spectrum (EDS) of the nanocomposite particles is in FIG. 8. The Cu peaks result from the sample grid. Spectral peaks that originate from the QD coating of the magnetic beads indicate the presence of Cd, Se, Zn, and S on the surface of the iron oxide particles. The relatively high Zn and S peaks could indicate the presence of multiple layers of ZnS on the surface of the CdSe QDs.[46-48]

Figure 9:
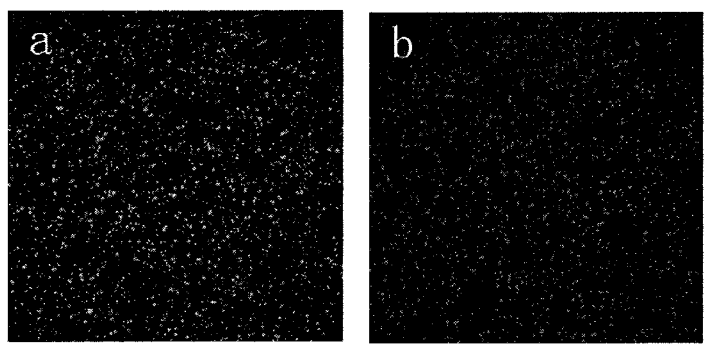
FIG. 9. Digital fluorescence microscopy images of magnetic beads coated with (a) 3 nm (green) and (b) 5 nm (red) CdSe/ZnS QDs.
Figure 10:
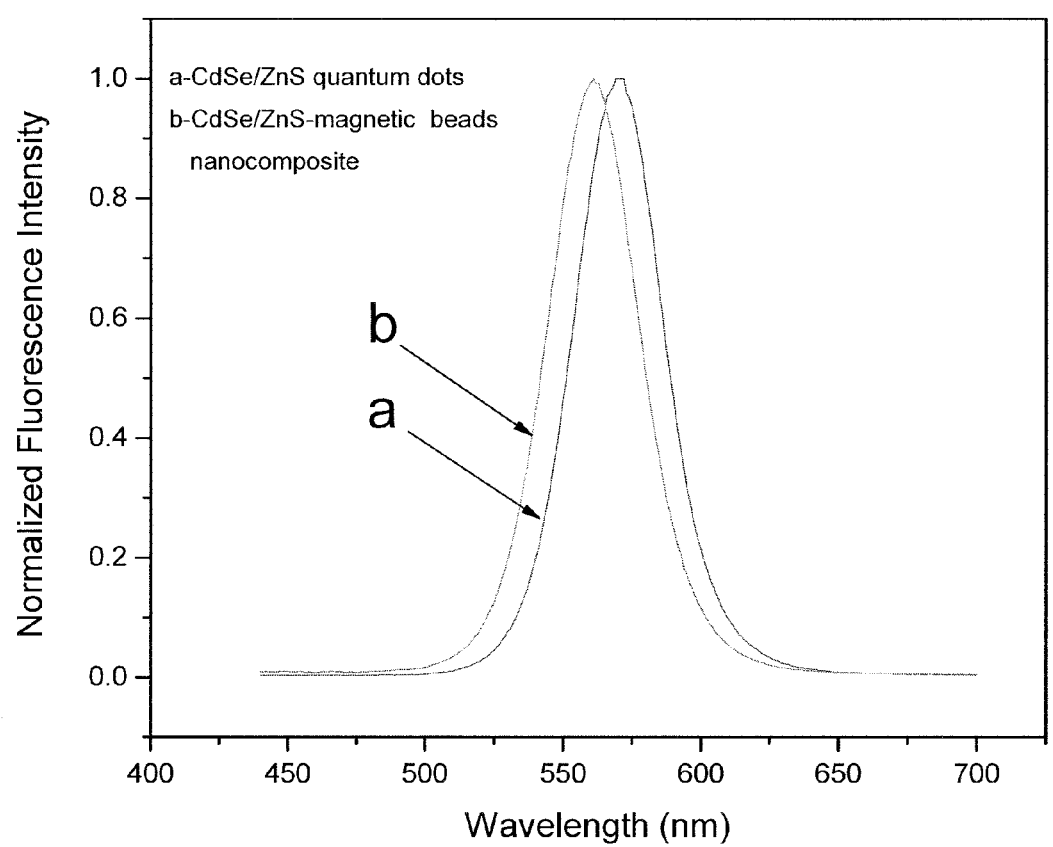
FIG. 10. Luminescence spectra. (a, red): CdSe/ZnS QDs in chloroform; (b, green): magnetic beads CdSe/ZnS QD core-shell nanoparticles in water.

Luminescence images of the nanocomposite particles coated with ~3 and ~5 nm CdSe/ZnS QDs are shown in FIGS. 9a and 9b, respectively. A large signal-to-background ratio of over 100 is observed in these digital images. No micrometric clusters of nanocomposite particles are seen. Luminescence spectra of CdSe/ZnS QDs in chloroform and CdSe/ZnS QDs-$\gamma$-$Fe_2O_3$ nanocomposite particles in aqueous solution are shown in FIG. 10. A slight blue shift is observed that could be attributed to a change in surface states of the QDs due to the immobilization. The emission quantum yield of the nanocomposite particles was found to be around 0.18, which is three times lower than the emission quantum yield of CdSe/ZnS QDs in chloroform (0.61). Luminescence lifetime of the luminescent/magnetic nanoparticles showed an excited-state lifetime of 65±5 ns. The excited-state lifetime of CdSe/ZnS nanoparticles was 27±3 ns. This excited-state lifetime of the CdSe/ZnS QDs was in agreement with previous studies.[49] It should be noted that the lifetime measurements yielded only approximate values since the fluorescence decay times exhibited significant variations from exponential decay curves. Nevertheless, the clear increase in excited state lifetime could be attributed to quenching interactions between the magnetic nanoparticles and the luminescent QDs or between the close packed QDs. The drop in the emission quantum yield could also be attributed to the solvent change and to possible changes in electronic density on the surface of the QDs due to their immobilization to the magnetic particles. While the ZnS capping passivates the surface of the CdSe QDs, the capping is not perfect. This could allow electrons to leak to the surface of the QDs and to the polymer coated magnetic core particle. Leakage of electrons from QDs has been previously observed when the surface of CdSe/ZnS QDs was modified with mercaptoacetic acid (or MPA, MUA).[39] This resulted in a decrease in the emission quantum yield and a blue shift in the emission spectrum of the modified QDs as observed in the experiments of the present inventors. It should be noted, however, that the width of the emission peak of the QDs was not affected by the coupling of QDs to the polymer-coated magnetic nanoparticles.

Figure 11:
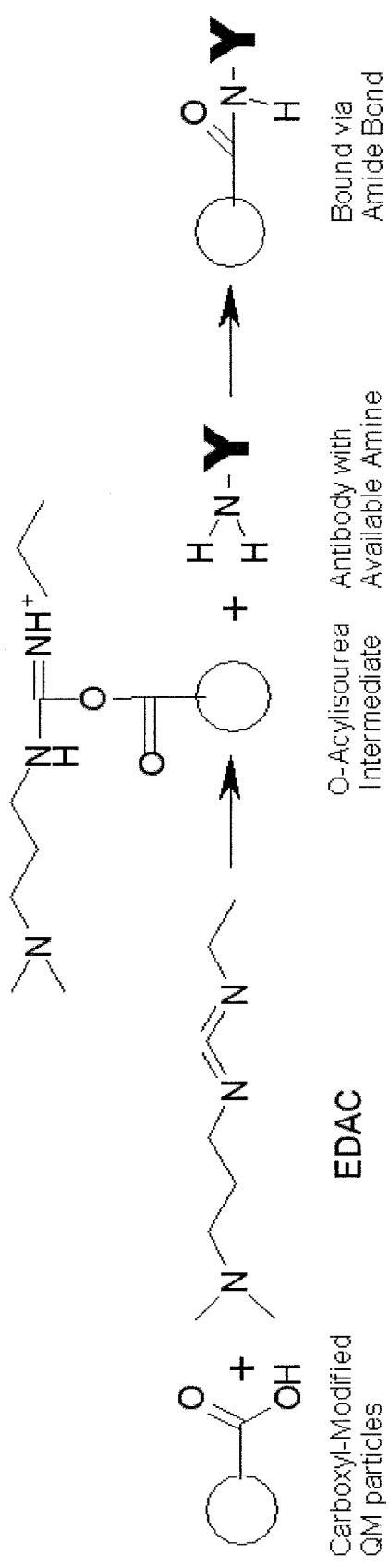
FIG. 11. Covalent attachment of anticycline E to the luminescent/magnetic particles using EDAC coupling chemistry.

To apply the luminescent/magnetic particles for magnetic separation of cells followed by luminescence detection, the present inventors first modified their surface with carboxylic functional groups. A 2 mL portion of 0.1 µM luminescent/magnetic nanoparticle suspension in methanol was transferred into a 250 mL flask, which was heated to 60° C. under stirring under reflux for 6 h. Then, 200 µl mercaptoacetic acid (Sigma) was injected into the flask. The reaction took 1 h to complete. The carboxyl-modified nanoparticles were washed three times using magnetic decantation and were finally dispersed in 2 mL deionized water and briefly vortexed to prevent aggregation. As expected, the carboxy-modified nanoparticles were highly water-soluble and also maintained their luminescence properties.[32,40] Mouse anticycline E antibody molecules were attached to the particles through EDAC (1-ethyl-3-(3-dimethylaminopropyl) carbodiimide) coupling as shown in FIG. 11.

Figure 12:
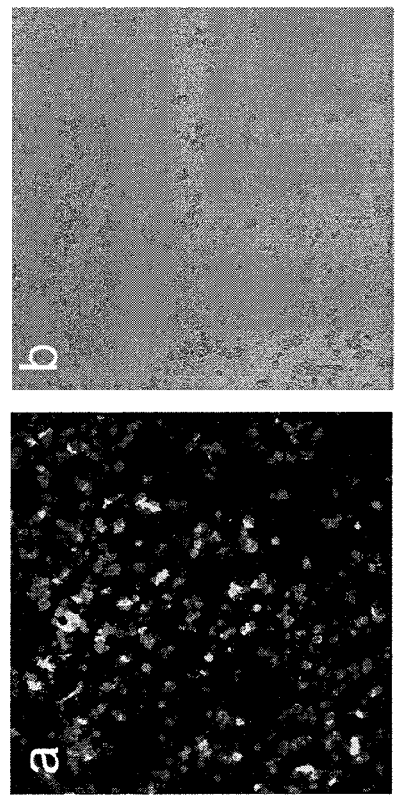
FIG. 12. 10× fluorescence (a) and transmission (b) microscopy images of anticycline E labeled luminescent/magnetic nanoparticles bound to MCF-7 breast cancer cells.

A 10 µl portion of mouse anticycline E antibody (Zymed) solution was added into 1 ml ~0.1 µM luminescent/magnetic nanoparticles suspension in a phosphate buffer (PB) solution at pH 7.4. Then 100 mg EDAC coupling reagent was added into the mixture. The mixture was gently shaken for 1 h and the antibody-labeled particles were then separated and washed using magnetic decantation. The anticycline E labeled nanoparticles were resuspended in 1 mL PB solution at pH 7.4. The use of EDAC coupling enabled the covalent attachment of the antibodies to the carboxyl-modified particles without substantially damaging the active site of the antibodies. To demonstrate the separation capability of the particles the present inventors incubated a sample of 200 µl anticycline E labeled luminescent/magnetic particles with a 1 mL MCF-7 breast cancer cell suspension containing 10,000 cells/mL. Following 15 min incubation at room temperature under gentle shaking the cells were separated from the suspension using a permanent magnet. The cells were washed twice with a phosphate buffer solution using magnetic decantation and observed using digital fluorescence imaging microscopy. Transmission and fluorescence images of the MCF-7 cells labeled with the anticycline E labeled particles are shown in FIG. 12. The cells were successfully pulled to the magnet, which meant that they were successfully bound to the anticycline E labeled particles. Control experiments with particles that were not labeled with anticycline E showed negligible nonspecific binding of the particles to MCF-7 cells. While free luminescent/magnetic particles were also pulled to the magnet, they could be easily distinguished from cells because of the 3-4 orders of magnitude size difference between the particles and the MCF-7 cells. The cell separation studies described here made use of a single antibody and luminescent QDs of a single emission color. The present inventors envision the use of luminescent/magnetic particles of different emission colors and different antibodies where the emission color would code for a specific antibody. This would enable the determination of multiple antigens on the cell surface, which could in turn increase the specificity of cancer diagnosis and staging. Currently the present inventors are characterizing the separation capability of the anticycline E labeled particles in mixtures containing MCF-7 and red blood cells. Preliminary measurements indicate that the technique can be used to separate 1 MCF-7 cell in 10 000 blood cells. However, the present inventors anticipate that technical improvements in the experimental system would increase the separation efficiency furthermore.

Conclusions. Water-soluble nanocomposite particles consisting of a magnetic core ($\gamma$-$Fe_2O_3$) and luminescent quantum dots shell (CdSe/ZnS QDs) were synthesized in an organic/water two-phase mixture. Thiol chemistry was used to bind the QDs to the surface of the magnetic beads. The luminescent/magnetic nanocomposite particles were characterized using TEM and EDS analysis. The particles averaged 20 nm in diameter with about 15% size variation, showed relatively smooth morphology, and were fully water miscible. They also exhibited high emission quantum yield and were easily separated from solution using a permanent magnet. Anticycline E molecules against the breast cancer specific marker cycline E, were attached to the luminescent/magnetic particles followed their functionalization with carboxylic groups through EDAC coupling. The anti cycline E labeled particles were used successfully to separate and detect breast cancer cells in serum. The separation capabilities of the antibody labeled particles in cell suspensions containing MCF-7 and red blood cells are currently under investigation.

REFERENCES (1) Murray, C. B.; Norris, D. J.; Bawendi, M. G. *J. Am. Chem. Soc.* 1993, 115, 8706.
(2) Hines, M. A.; Guyot-Sionnest, P. *J. Phys. Chem.* 1996, 100, 468.
(3) Dabbousi, B. O.; Rodriguez-Viejo, J.; Mikulec, F. V.; Heine, J. R.; Mattoussi, H.; Ober, R.; Jensen, K. F.; Bawendi, M. G. *J. Phys. Chem. B* 1997, 101, 9463.
(4) Peng, X.; Wickham, J.; Alivisatos, A. P. *J. Am. Chem. Soc.* 1998, 120(21), 5343.
(5) Peng, Z. A.; Peng, X. *J. Am. Chem. Soc.* 2001, 123(1), 183.
(6) Barbera-Guillem, E. Published patent application no. US 2002001716 A, 2001.
(7) Rogach, A. L.; Nagesha, D.; Ostrander, J. W.; Giersig, M.; Kotov, N. A. *Chem. Mater.* 2000, 12, 2676.
(8) Moffitt, M.; Vali, H.; Eisenberg, A. *Chem. Mater.* 1998, 10, 1021.
(9) Chen, Y.; Rosenzweig, Z. *Nano Lett.* 2002, 2(11), 1299.
(10) Decher, G.; Hong, J. D. *Makromol. Chem. Macromol. Symp.* 1991, 46, 321.
(11) Decher, G.; Hong, J. D.; Schmitt, J. *Thin Solid Films* 1992, 210/211, 831.
(12) Anzai, J.; Hoshi, T.; Nakamura, N.; *Langmuir* 2000, 16(15), 6306.
(13) Caruso, F.; Trau, D.; Mohwald, H.; Renneberg, R.; *Langmuir* 2000, 16(4), 1485.
(14) Goldman, E. R.; Balighian, E. D.; Mottoussi, H.; Kuno, M. K.; Mauro, J. M.; Tran, P. T.; Anderson, G. P. *J. Am. Chem. Soc.* 2002, 124, 6378.
(15) Pathak, S.; Choi, S.-K.; Arnheim, N.; Thompson, M. E. *J. Am. Chem. Soc.* 2001, 123(17), 4103.
(16) Willard, D. M.; Carillo, L. L.; Jung, J.; Van Orden, A. *Nano Lett.* 2001, 1(9), 469.
(17) Qu, L.; Peng, X. *J. Am. Chem. Soc.* 2002, 124(9), 2049.
(18) Rebizak, R.; Schaefer, M.; Dellacherie, E. *Bioconjugate Chem.* 1997, 8(4), 605.
(19) Striolo, A.; Ward, J.; Prausnitz, J. M.; Parak, W. J.; Zanchet, D.; Gerion, D.; Milliron, D.; Alivisatos, A. P. *J. Phys. Chem. B* 2002, 106(21), 5500.
(20) Ballerstadt, R.; Schultz, J. S. *Anal. Chem.* 2000, 72(17), 4185.
(21) Lis, H.; Sharon, N. *Chem. Rev.* 1998, 98(2), 637.
(22) Alivisatos, A. P. *Science* 1996, 217, 933.
(23) Murray, C. B.; Norris, D. J.; Bawendi, M. G. *J. Am. Chem. Soc.* 1993, 115, 8706-8715.
(24) Donega', C. M.; Hickey, S. G.; Wuister, S. F.; Vanmaekelbergh, D.; Meijerink, A. *J. Phys. Chem. B* 2003, 107, 489-496.
(25) Peng, Z. A.; Peng, X. *J. Am. Chem. Soc.* 2001, 123, 183-184.
(26) Cohen, R.; Kronik, L.; Shanzer, A.; Cahen, D.; Liu, A.; Rosenwaks, Y.; Lorenz, J. K.; Ellis, A. B. *J. Am. Chem. Soc.* 1999, 121, 10545-10553.
(27) Murray, C.; Kagan, C.; Bawendi, M. *Annu. Rev. Mater. Sci.* 2000, 30, 546-610.
(28) Brus, L. *Appl. Phys. A.* 1991, 53, 465-474.
(29) Warren, C. W.; Nie, S. *Science* 1998, 281, 2016-2018.
(30) Nazzal, A. Y.; Qu, L.; Peng, X.; Xiao, M. *Nano Lett.* 2003, 3, 819-822.
(31) Dabbousi, B. O.; Rodriguez-Viejo, J.; Mikelec, F. V.; Heine, J. R.; Mattoussi, H.; Ober, R.; Jensen, K. F.; Bawendi, M. G. *J. Phys. Chem. B* 1997, 101, 9463-9475.
(32) Gerion, D.; Pinard, F.; William, S. C.; Parak, W. J.; Zanchet, D.; Weiss, S.; Alivisatos, A. P. *J. Phys. Chem. B* 2001, 105, 8861-8871.
(33) Barbara-Guillem, E. US 2002001716 A, 2001.
(34) Chen, Y.; Rosenzweig, Z. *Nano Lett.* 2002, 2, 1299-1302.
(35) Chen, Y.; Ji, T.; Rosenzweig, Z. *Nano Lett.* 2003, 3, 581-584.
(36) Wang, Y. A.; Li, J. J.; Chen, H.; Peng, X. *J. Am. Chem. Soc.* 2002, 124, 2002.
(37) Zhang, C.; O'Brien, S.; Balogh, L. *J. Phys. Chem. B* 2002, 106, 10316-10321.
(38) http://www.indicia.fr.
(39) Wuister, S. F.; Swart, I.; Driel, F. V.; Hickey, S. G.; Donega', C. M. *Nano Lett.* 2003, 3, 503-507.
(40) Aldana, J.; Wang, Y. A.; Peng, X. *J. Am. Chem. Soc.* 2001, 123, 8844-8850.
(41) Harruff, B. A.; Bunker, C. E. *Langmuir* 2003, 19, 893-897.
(42) Guo, W.; Li, J. J.; Wang, Y. A.; Peng, X. *J. Am. Chem. Soc.* 2003, 125, 3901-3909.
(43) Wang, Y. A.; Li, J. J.; Chen, H.; Peng, X. *J. Am. Chem. Soc.* 2002, 124, 2002.
(44) Zhang, C.; O'Brien, S.; Balogh, L. *J. Phys. Chem. B* 2002, 106, 10316-10321.
(45) Cohen, R.; Kronik, L.; Shanzer, A.; Cahen, D.; Liu, A.; Rosenwaks, Y.; Lorenz, J. K.; Ellis, A. B. *J. Am. Chem. Soc.* 1999, 121, 10545-10553.
(46) Cumberland, S. L.; Berrettini, M. G.; Javier, A.; Strouse, G. F. *Chem. Mater.* 2003, 15, 1047-1056.
(47) Hines, M. A.; Guyot-Sionnest, P. *J. Phys. Chem.* 1996, 100, 468-471.

(48) Van Sark, W. G. J. H. M.; Frederix, P. L. T. M.; Van den Heuvel, D. J.; Gerritsen, H. C.; Bol, A. A.; van Lingen, J. N. J.; de Mello Donega, C.; Meijerink, A. *J. Phys. Chem. B* 2001, 105, 8281-8284.

(49) Fisher, B. R.; Hans-Jurgen, E.; Nathan, E. S.; Bawendi, M. G. *J. Phys. Chem. B* 2003, 108, 143-148.

Incorporated herein by reference is "Synthesis of Glyconanospheres Containing Luminescent CdSe—ZnS Quantum Dots" by Yongfen Chen, Tianhao Ji, and Zeev Rosenzweig, published in *Nano Lett.*, Vol. 3, No. 5, 2003, 581-584 (copy attached to U.S. Provisional Patent Application Ser. No. 60/555,629, filed 23 Mar. 2004).

Also incorporated herein by reference is "Superparamagnetic $Fe_2O_3$ Beads-CdSe/ZnS Quantum Dots Core-Shell Nanocomposite Particles for Cell Separation" by Desheng Wang, Jibao He, Nista Rosenzweig, and Zeev Rosenzweig, published in *Nano Lett.*, 2004, Vol. 4, No. 3, 409-413 (copy attached to U.S. Provisional Patent Application Ser. No. 60/555,629, filed 23 Mar. 2004).

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. Luminescent and magnetic nanoassemblies comprising luminescent semiconductor quantum dots ("QDs") and magnetic nanoparticles, wherein components in the nanoassemblies are bound covalently.

2. The nanoassemblies of claim 1, in which luminescent quantum dots of around 1-5 nm in diameter directly coat core magnetic nanoparticles of around 10-20 nm in diameter.

3. The nanoassemblies of claim 1, in which luminescent quantum dots and magnetic nanocrystals are assembled in glyconanospheres.

4. The nanoassemblies of claim 1, wherein the nanoassemblies are encapsulated in glyconanospheres.

5. The nanoassemblies of claim 1, comprising luminescent semiconductor Cd-containing QDs and magnetic nanoparticles.

6. The nanoassemblies of claim 1, wherein the QDs include a shell of ZnS.

7. The nanoassemblies of claim 1, wherein the magnetic nanoparticles are magnetic iron oxide nanoparticles.

8. The nanoassemblies of claim 1, comprising luminescent semiconductor Cd-containing QDs and magnetic nanoparticles comprising iron oxide.

9. The nanoassemblies of claim 1, comprising luminescent semiconductor CdSe—ZnS QDs and magnetic iron oxide nanoparticles.

10. The nanoassemblies of claim 1, wherein the nanoassemblies comprise QDs bound to the surface of thiol-modified magnetic nanoparticles.

11. The nanoassemblies of claim 1, wherein some of the components in the nanoassemblies are bound electrostatically.

12. The nanoassemblies of claim 1, wherein the nanoassemblies contain molecules on their surface that interact strongly with carbohydrate binding proteins.

13. The nanoassemblies of claim 12, wherein the molecules are dextran molecules.

14. The nanoassemblies of claim 1, wherein the nanoassemblies contain molecules on their surface that interact with protein binding carbohydrates.

15. A plurality of the nanoassemblies of claim 1, averaging around 200 nm±25 nm in diameter or smaller.

16. A plurality of the nanoassemblies of claim 1, averaging around 30 nm±15% in diameter or smaller.

17. A plurality of the nanoassemblies of claim 1, averaging around 20 nm±15% in diameter or smaller.

18. A plurality of the nanoassemblies of claim 1, averaging around 20 nm±15% in diameter.

19. A method of assembling luminescent semiconductor quantum dots ("QDs") and magnetic nanoparticles into the nanoassemblies of claim 1, comprising:
   providing luminescent semiconductor QDs in chloroform;
   providing magnetic nanoparticles in water;
   coupling the QDs to the magnetic nanoparticles in a chloroform/methanol/water mixture.

20. The method of claim 19, wherein:
   methanol is added to the QD-containing chloroform to form a mixture of methanol and QD-containing chloroform; and
   the water containing magnetic nanoparticles is injected into the mixture of methanol and QD-containing chloroform under sonication and vigorous stirring.

21. The method of claim 19, wherein the QDs comprise highly luminescent semiconductor CdSe—ZnS and the magnetic nanoparticles comprise iron oxide nanoparticles.

22. A method of using the nanoassemblies of claim 1 for real-time monitoring of protein-carbohydrate interactions, comprising:
   attaching to the nanoassemblies a protein or carbohydrate to create modified nanoassemblies;
   exposing the modified nanoassemblies to fluid thought to contain a carbohydrate or protein of interest to allow protein-carbohydrate interactions to occur if the fluid contains the carbohydrate or protein of interest;
   observing the modified nanoassemblies after the modified nanoassemblies are exposed to the fluid.

23. The method of claim 22, wherein the modified nanoassemblies are separated from the fluid using magnetic force.

24. A method of using the nanoassemblies of claim 1 for detecting cancer cells, comprising:
   attaching to the nanoassemblies antibodies against membranal biomarkers that are selectively expressed in breast cancer cells to create modified nanoassemblies;
   exposing the modified nanoassemblies to fluid thought to contain circulating breast cancer cells to allow the modified nanoassemblies to attach selectively to any breast cancer cells through binding of the antibody-modified nanoassemblies to membranal biomarkers on the cancer cells.

25. The method of claim 24, wherein the modified nanoassemblies are separated from the fluid using magnetic force.

26. The method of claim 24, wherein the fluid includes blood which contains breast cancer cells, and the breast cancer cells bound to the modified nanoassemblies are separated from the blood using magnetic force.

27. The method of claim 24, wherein the modified nanoassemblies have different emission colors and different antibodies where the emission color would code for a specific antibody, to enable determination of multiple biomarkers on a cell surface.

* * * * *